(12) United States Patent
Satou et al.

(10) Patent No.: US 6,367,327 B2
(45) Date of Patent: Apr. 9, 2002

(54) METHOD AND APPARATUS FOR INSPECTING COMMUNICATING HOLE OF A CAST MOLDED ARTICLE

(75) Inventors: Miyuki Satou, Toyota; Oscar Vanegas, Nagoya; Toyokazu Itou, Nissin, all of (JP)

(73) Assignee: Ryoei Engineering Co., Ltd. (JP)

( * ) Notice: Subject to any disclaimer, the term of this patent is extended or adjusted under 35 U.S.C. 154(b) by 0 days.

(21) Appl. No.: 09/778,090

(22) Filed: Feb. 7, 2001

(30) Foreign Application Priority Data

May 19, 2000 (JP) .......................... 2000-147624

(51) Int. Cl.$^7$ .............................................. G01N 29/14
(52) U.S. Cl. ............................. 73/587; 73/602; 73/659; 73/116; 73/579
(58) Field of Search .................. 73/587, 579, 597, 73/598, 599, 600, 602, 648, 659, 116, 117.2, 117.3, 118.1, 35.01, 35.03, 35.06, 35.07, 35.09

(56) References Cited

U.S. PATENT DOCUMENTS

| | | | | |
|---|---|---|---|---|
| 3,974,680 A | * | 8/1976 | Beaver | ................... 73/40.5 R |
| 4,252,013 A | * | 2/1981 | Hyanova et al. | ........... 73/117.3 |
| 4,520,660 A | * | 6/1985 | Hitchcock | .................... 73/120 |
| 4,587,838 A | * | 5/1986 | Sakai et al. | .................... 73/116 |
| 5,272,911 A | * | 12/1993 | Beggs et al. | .................. 73/49.7 |
| 5,392,642 A | * | 2/1995 | Tao | ........................... 73/117.3 |
| 5,744,705 A | * | 4/1998 | Deroen et al. | ................ 73/116 |

FOREIGN PATENT DOCUMENTS

| | | | | |
|---|---|---|---|---|
| JP | 59085954 | * | 5/1984 | .................. 73/579 |
| JP | 7-63541 | | 3/1995 | |
| JP | 2000-338090 | | 12/2000 | |

\* cited by examiner

Primary Examiner—Hezron Williams
Assistant Examiner—Jacques Saint-Surin
(74) Attorney, Agent, or Firm—Parkhurst & Wendel, L.L.P.

(57) ABSTRACT

A transmitter of audible sound waves is disposed at one end of a communicating hole of a cast molded article such as a cylinder block, and a receiver of audible sound waves is disposed at the other end of the communicating hole. The quality of the communicating hole is determined by receiving audible sound waves from a transmitter which have passed through the communicating hole and computing and processing a frequency spectrum of the received audible sound waves based on a reference frequency spectrum.

11 Claims, 9 Drawing Sheets

METHOD AND APPARATUS FOR INSPECTING COMMUNICATING HOLE OF A CAST MOLDED ARTICLE

BACKGROUND OF THE INVENTION

1. Field of the Invention

The present invention relates to a method and apparatus for inspecting a communicating hole of a cast molded article for inspecting the degree of obstruction of a communicating hole formed in a cast molded article, and more particularly relates to a method and apparatus for inspecting a communicating hole of a cast molded article suitable for inspecting the degree of obstruction of a communicating hole for cooling water formed within a cast molded article such as a cylinder block of an engine.

2. Description of the Related Art

A cast molded article such as a cylinder block or a cylinder head of an automobile is provided with a network of communicating holes therein for cooling water. These communicating holes are formed by arranging a core within a mold. However, there are cases in which heat and the flow of molten metal during cast molding cause the core to crack and break, obstructing the communicating hole and making it narrow. Since this type of defect may lead to poor cooling, poor engine efficiency, and seizure of the engine, it is necessary to inspect the communicating holes of all products after cast-molding. However, because the communicating holes of which there is a complex network inside cast molded articles twist and bend, they can not be directly visually checked for defects as can be linear communicating holes.

Therefore, the quality of communicating holes is determined using various means such as by manually shining a light into the opening of a communicating hole and looking at the reflected light that passes through to the other end, or by passing a wire or the like through the communicating hole. The quality of complex communicating holes is determined using such means as an endoscopic light source capable of bending at the end or observing the inside with optic fiber. However, with the method of passing a wire through the communicating hole it was difficult not only to pass the wire through a communicating hole, but also to know just how narrow the communicating hole was. Moreover, the operation was troublesome. Also, an endoscope and optic fiber were not able to be inserted all the way into the inner portion of complex communicating holes and much manual labor was required.

In an attempt to automate inspection, investigations have also been made into detecting light illuminated into a communicating hole from an opening thereof with an optical sensor disposed at an adjoining communicating hole opening, as well as feeding air into a communicating hole from an opening thereof and detecting the air pressure and air flow rate at an adjoining communicating hole opening. However, because the inside of a communicating hole changes color and its surface becomes rough, light passed through a communicating hole attenuates to 1/100 or less, so that sufficient determination can not be made. Also, with the air method, due to the fact that air leaks from other communicating holes that branch off, the air pressure attenuates to 1/1000 or less at the branching point, so that sufficient determination can not be made. Therefore, practical application of either of these methods was difficult. In addition, it is necessary to fit the air feed hole and pressure sensor tightly against the communicating hole opening during measuring so air does not leak, as well as have the light source and light sensor as close as possible to the communicating hole opening in order to inhibit attenuation. These make setup prior to measuring troublesome and time consuming.

SUMMARY OF THE INVENTION

The object of the present invention is to provide a method and apparatus for inspecting a communicating hole of a cast molded article which enables reliable determination of the quality of a communicating hole of a complex shape formed in a cast molded article.

A first aspect of the present invention is a method of inspecting a communicating hole of a cast molded article, in which audible sound waves are emitted into one end of a communicating hole of a cast molded article and the audible sound waves which passed through the communicating hole are received at the other end thereof. The frequency spectrum of the received audible sound waves are then computed and processed based on a reference frequency spectrum, such that the quality of the communicating hole is determined.

Also, a second aspect of the present invention is an apparatus for inspecting a communicating hole of a cast molded article, provided with an audible sound wave transmitter disposed at one end of the communicating hole of a cast molded article, an audible sound wave receiver disposed at the other end of the communicating hole for receiving the audible sound waves sent from the transmitter which has passed through the communicating hole, and a computing and processing device for determining the quality of the communicating hole by computing and processing the frequency spectrum of the audible sound waves received by this receiver based on a reference frequency spectrum.

Further, in the first and second aspects above, the audible sound waves from the transmitter are able to be swept from a low frequency to a high frequency or from a high frequency to a low frequency. It is preferable to use audible sound waves of a frequency of 1 to 20,000 Hz. A plurality of transmitters and/or receivers may be provided.

Moreover, the above-mentioned computing and processing in the first and second aspects enables the frequency spectrum of the received audible sound waves to be computed and processed by a neural network.

DETAILED DESCRIPTION OF THE PREFERRED EMBODIMENTS

Next, preferred embodiments of the present invention will be described in detail. In this embodiment, the cast molded article is a cylinder head S, with water holes which are non-linear communicating holes formed therein being the subject of inspection.

Figure 1:
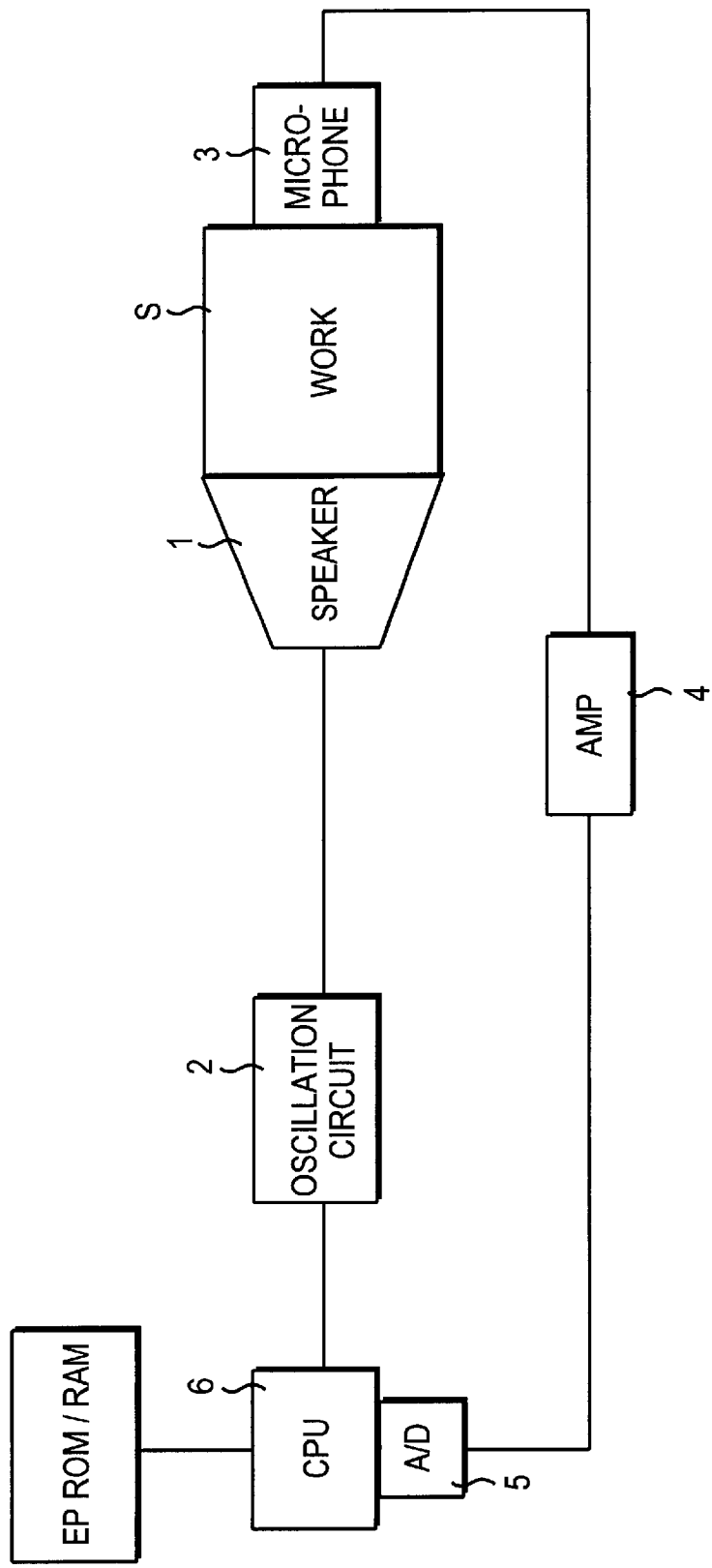
FIG. 1 is a block diagram illustrating a preferred embodiment of the present invention.

FIG. 1 shows a configuration of the apparatus of the present invention. As shown in this figure, a transmitter 1 such as a speaker for transmitting audible sound waves is provided at an open end of a communicating hole formed in one end of a cylinder head S which is a cast molded article. Also, a receiver 3 such as a microphone is provided at the other end of the opening in the cylinder head S. The received audible sound waves are converted into an electrical signal and amplified with an amplifier 4, after which they are converted into a digital signal by means of an A/D converter 5 and then input to a computing and processing device 6. As shown in FIG. 1, EPROM and RAM are connected to this computing and processing device 6. After being digitized via A/D conversion, the audible sound waves are temporarily stored in RAM. A calculation formula of the neural network, which will be mentioned later, and "weights", operation algorithm, swept frequency data and the like at each point of waveform of the frequency spectrum are stored in EPROM.

Figure 2:
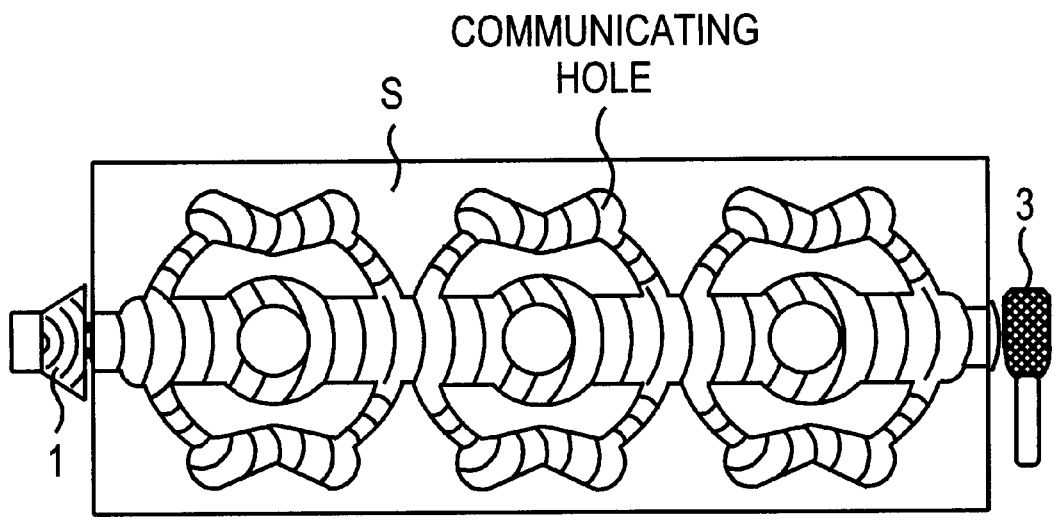
FIG. 2 is a schematic view showing a communicating hole in a good cylinder block.
Figure 3:
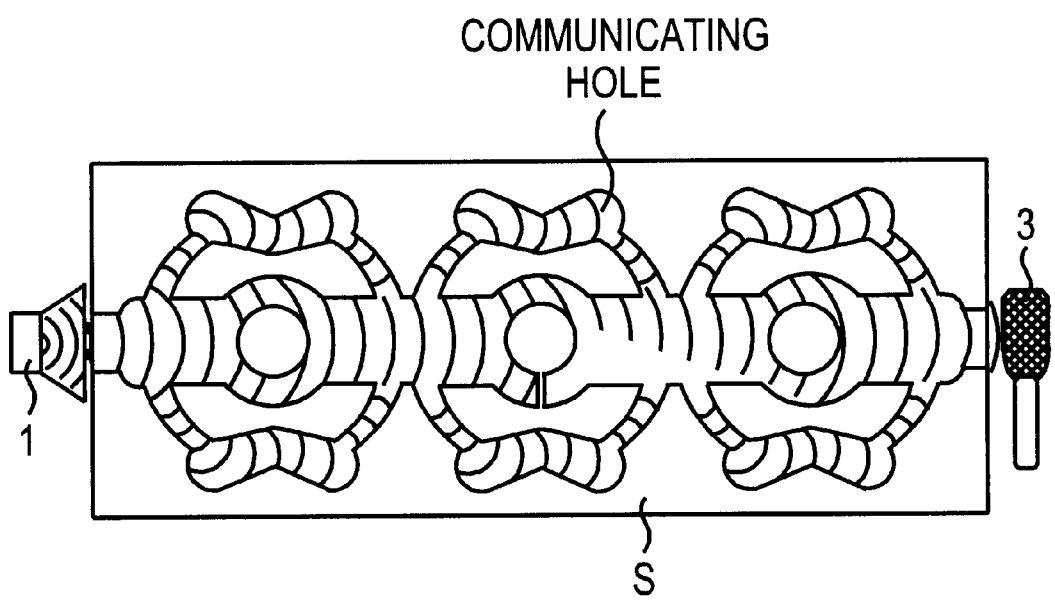
FIG. 3 is a schematic view showing a communicating hole in a bad cylinder block.

The transmitter 1 is connected to an oscillation circuit 2, which transmits audible sound waves of a frequency swept from 1 to 6,000 Hz, for example. The audible sound waves transmitted from one of the openings of the communicating hole proceeds inside the communicating hole, as shown in FIGS. 2 and 3, toward the other opening of the communicating hole. Inside a non-linear communicating hole, the audible sound waves reverberate, resonate, or directly reach the other end of the opening. The audible sound waves of the swept frequency are then received via a receiver 3 provided at the opening at the other end of the cylinder head S. Audible sound waves of 1 to 20,000 Hz may also be used depending on the diameter of the communicating hole. Note that FIG. 2 shows a communicating hole of a good cylinder block and FIG. 3 shows a communicating hole of a bad cylinder block.

In this embodiment, the frequency is swept such that audible sound waves of 1 to 6,000 Hz go from a low frequency to a high frequency. Conversely, the frequency may also be swept from high to low such that the audible sound waves go from 6,000 to 1 Hz. A plurality of open ends at one end of a cylinder head S may be provided with a plurality of transmitters 1 from where swept audible sound waves are transmitted. In this case, the swept audible sound waves sent from each transmitter 1 are received by a single receiver 3 provided at the opening at the other end of the cylinder heads. They may be received by the receivers 3 corresponding to the number of transmitters 1 provided at the open end at the other end of the cylinder head. This makes it possible to improve detection accuracy. Furthermore, inspection may be conducted with a plurality of transmitters 1 and receivers 3 disposed at branching passages or the like within the communicating hole.

The receiver 3 detects the audible sound waves sent from the transmitter 1 when they are propagated through the communicating hole. Of the audible sound waves which have passed through the communicating hole, there are those which have reached the opening of the communicating hole directly, those which have reached the opening of the communicating hole after reverberating repeatedly, and those which have reached the opening of the communicating hole after resonating therein. Accordingly, these sound waves contain information about the communicating hole. It is thus possible to know the state of the inside of the communicating hole by analyzing these sound waves. In addition, if there is a large amount of noise in the detected frequency spectrum, a filter can be used to eliminate the noise and reshape the waveforms.

Figure 12:
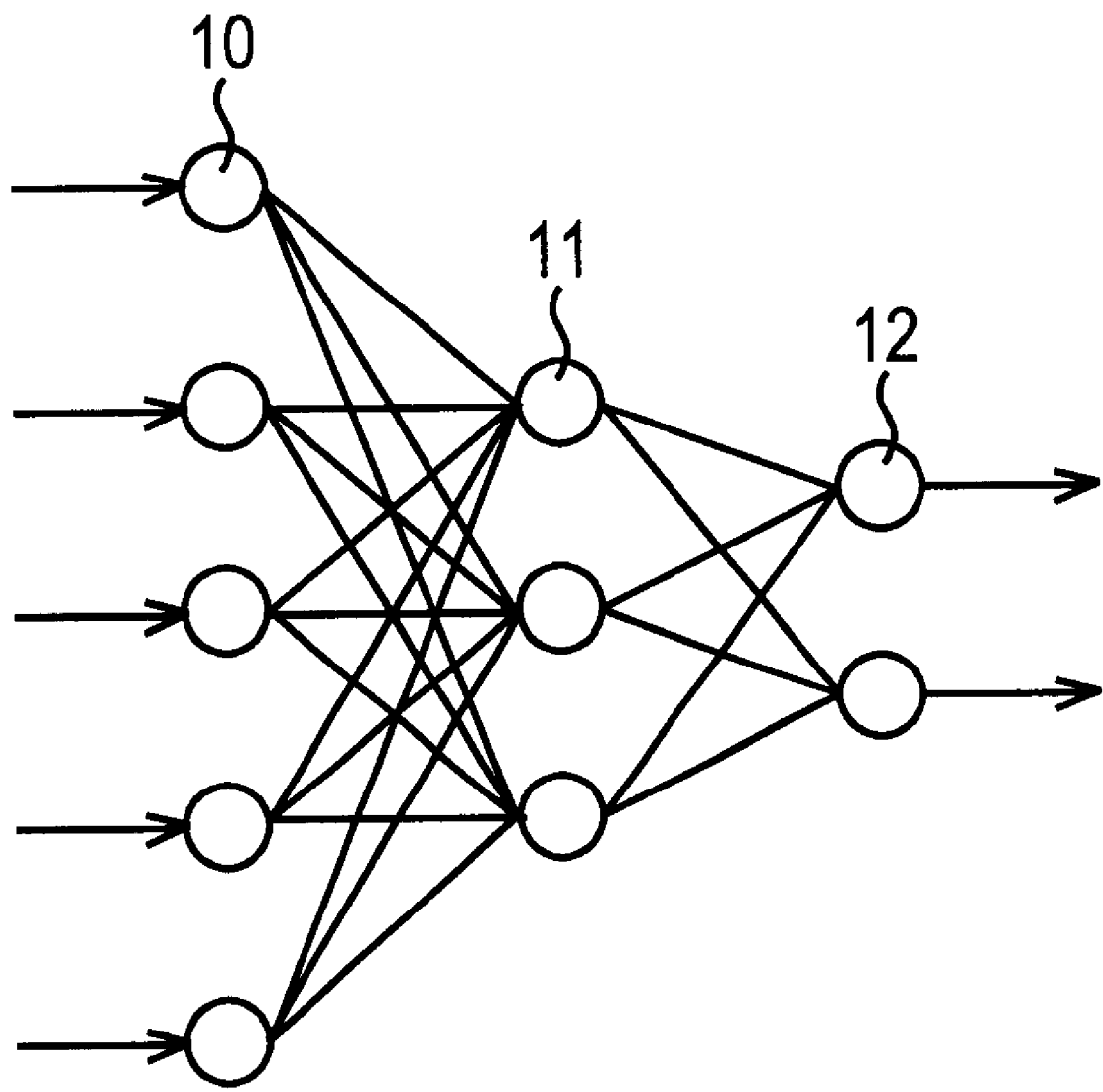
FIG. 12 is a basic illustration of the neural network.

In this embodiment, the computing and processing device 6 computes and processes the frequency spectrum of the received audible sound waves via a neural network so as to determine the quality of the communicating hole. Quality determination by the neural network is conducted via Back-Propagation (Error-Back-Propagation Method) formed of an input layer 10, a middle layer 11, and an output layer 12, as shown in the basic illustration of FIG. 12. Note that the output layer 12 is formed of an output layer 12a as a good product and an output layer 12b as a bad product. Output layers 12a and 12b both output values from "0" to "1" as their output values. With Back-Propagation learning is conducted based on inspected good and bad cylinder heads S. With a good cylinder head S, the output value from the output layer 12a as a good product converges on a target value of "1". With a bad cylinder head S, "weights" are obtained such that the output value from the output layer 12b as a bad product converges on a target value of "1". Therefore, these output values indicate the probability of the inspected product being either good or bad. A "1" for these output values corresponds to the inspected product being either good or bad. It can therefore be determined that the closer the output value of the output layer 12a as a good product is to the target value of "1", the higher the probability that the inspected product is good. And the closer the output value of the output layer 12b as a bad product is to the target value of "1" the higher the probability that the inspected product is bad.

That is, the above-mentioned "weights" are obtained through the learning process of the neural network. In a good group of inspected products, "weights" are learned and obtained such that the output value from the output layer 12a as a good product converges on the target value of "1". In a bad group of inspected products (1), "weights" are learned and obtained such that the output value from the output layer 12b as a bad product converges on the target value of "1". At this time, with a bad product in which the type of defect of the communicating hole differs from that of the bad product group (1), a bad product group (2) of that type learns and obtains "weights" such that the output value from the output layer 12b as a bad product converges on the target value of "1". That is, in inspecting for good and bad products, the "weight" data at each point of the waveform of the frequency spectrum becomes the reference frequency spectrum such that the output layer 12a as a good product and the output layer 12b as a bad product each converge on a target value of "1".

Figure 4:
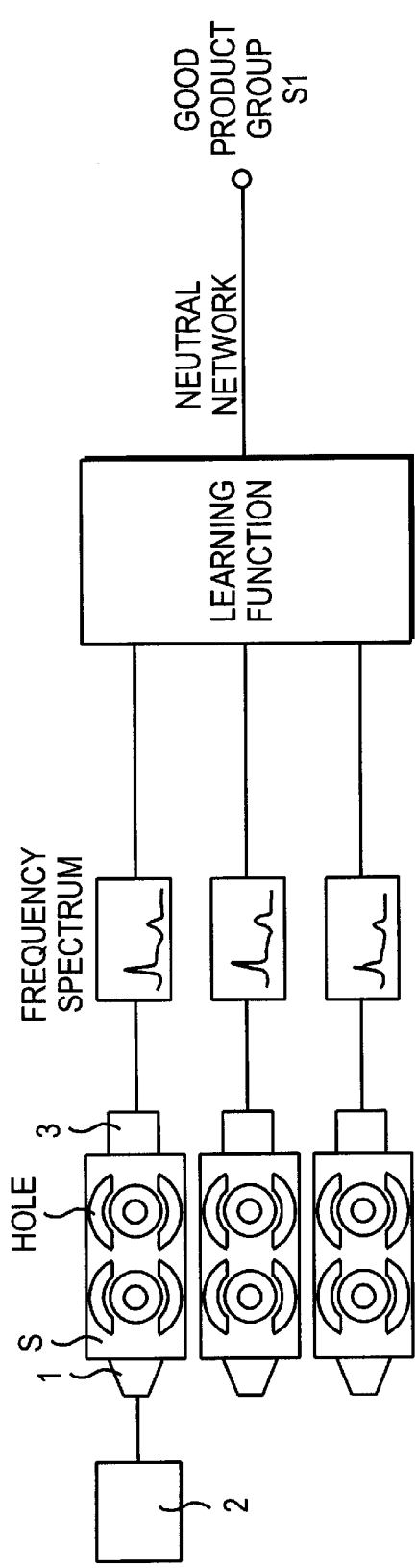
FIG. 4 is an explanatory view of a state in which a neural network learns a good product.
Figure 5:
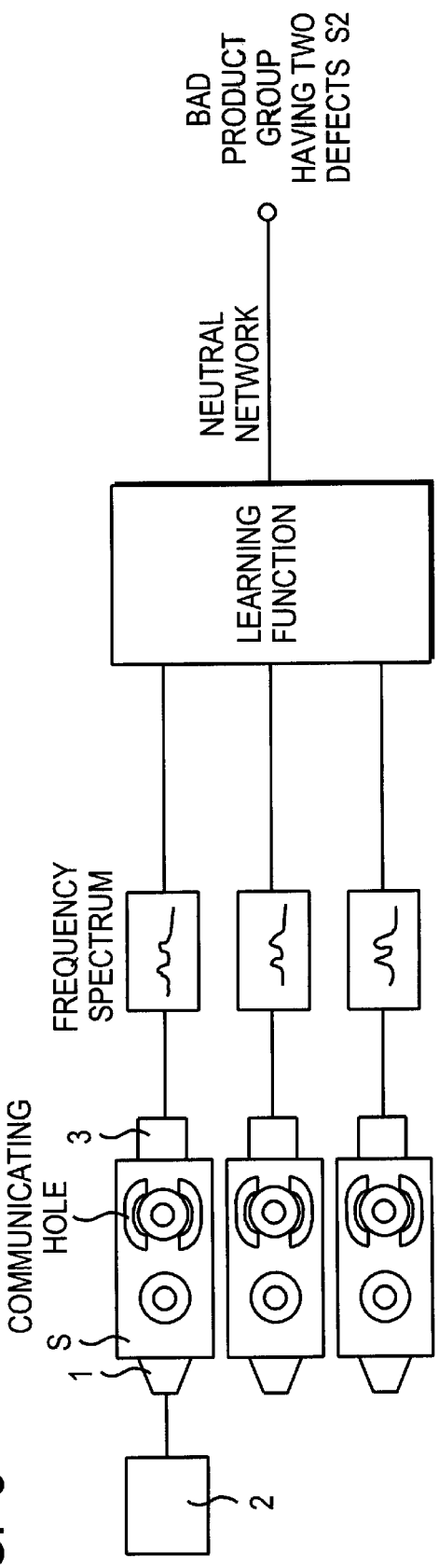
FIG. 5 is an explanatory view of a state in which the neural network learns a bad product with two defects in a communicating hole.
Figure 6:
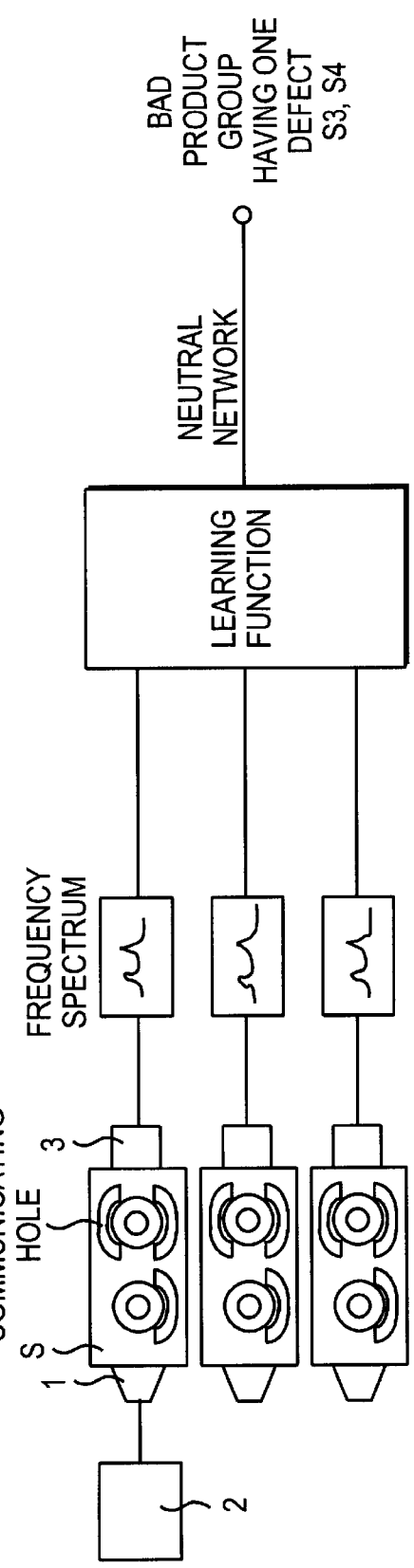
FIG. 6 is an explanatory view of a state in which the neural network learns a bad product with one defect in a communicating hole.
Figure 8:
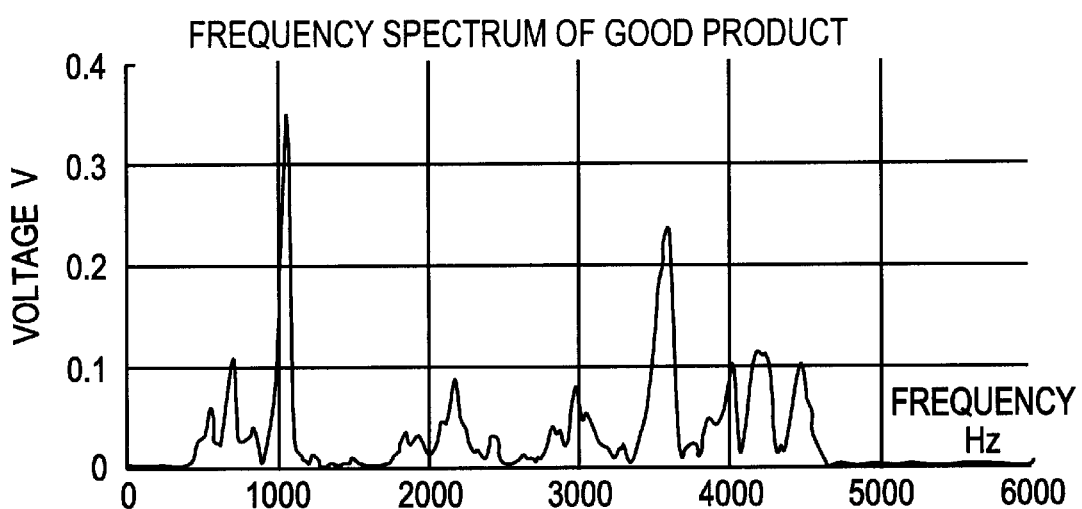
FIG. 8 is a graph showing a frequency spectrum of a good product.
Figure 9:
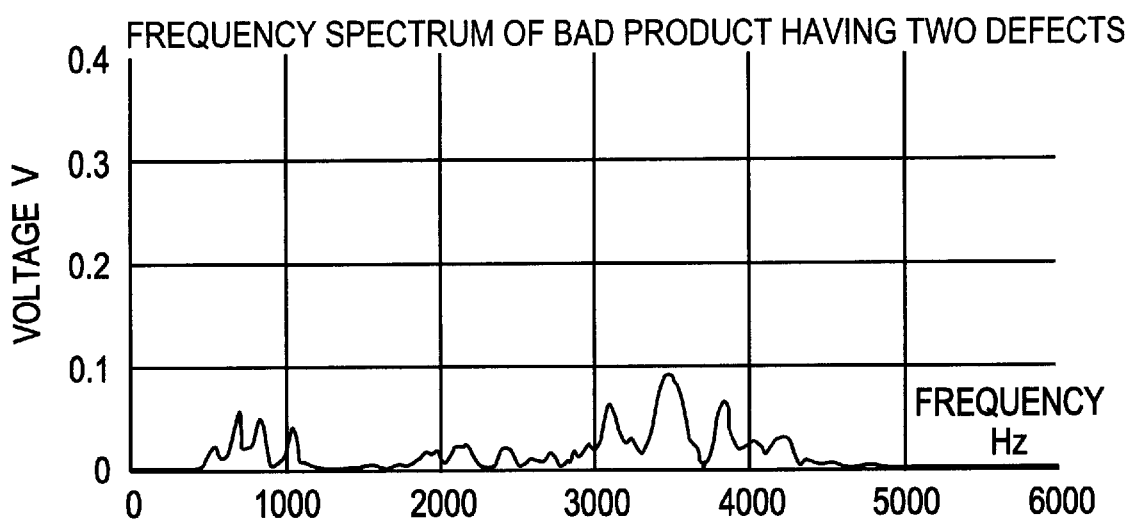
FIG. 9 is a graph showing a frequency spectrum of a bad product with two defects in a communicating hole.

More specifically, with a good cast molded article, the detected frequency spectrum will have two sizeable peaks, as shown in FIG. 8. At this time the output layer 12a as a good product of the neural network outputs a value close to the target value "1". A cylinder head S1 group having this type of good product frequency spectrum is learned, as shown in FIG. 4, and "weights" are obtained. The frequency spectrum which has been "weighted" this type of good product is used as a reference frequency spectrum. Also, with a bad product having two defects, the detected frequency spectrum will have no peaks, as shown in FIG. 9. At this time, the output layer 12b as a bad product of the neural network outputs a value close to the target value of "1". A cylinder head S2 group having this type of bad product frequency spectrum is learned, as shown in FIG. 5, and "weights" are obtained. The frequency spectrum which has been "weighted" this type of bad product is used as a reference frequency spectrum. Also, with the bad product groups S3 and S4 each having one defect, the detected frequency spectrums become the spectrums shown in FIGS. 10 and 11, respectively. At this time, the output layer 12b for a bad product of the neural network outputs a value close to the target value of "1". Cylinder head S3 and S4 groups having this type of bad product frequency spectrums are learned, as shown in FIG. 6, respectively, and "weights" are obtained. The frequency spectrum which has been "weighted" this type of bad product is used as a reference frequency spectrum.

Figure 10:
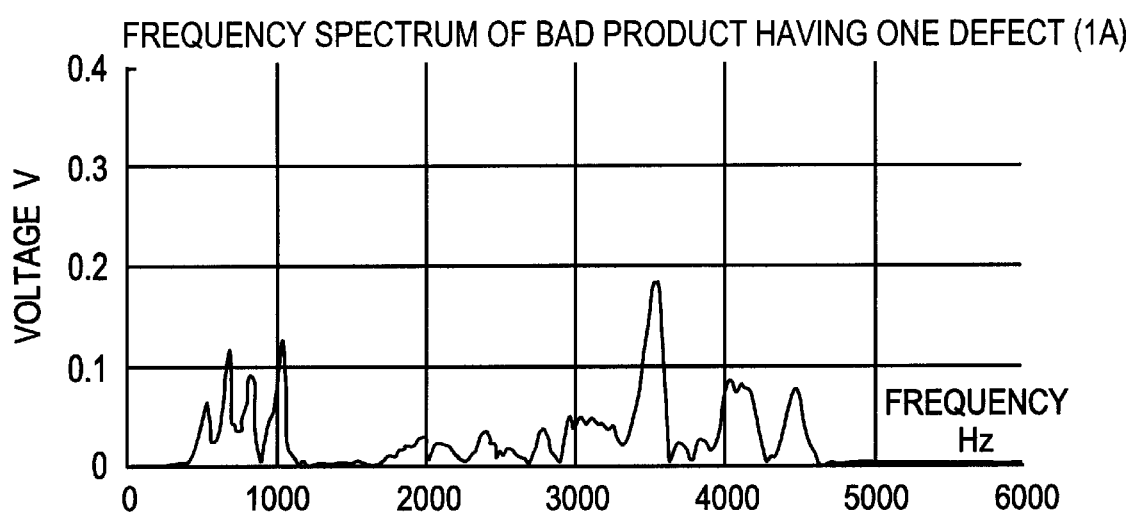
FIG. 10 is a graph showing a frequency spectrum of a bad product with one defect in a communicating hole.
Figure 11:
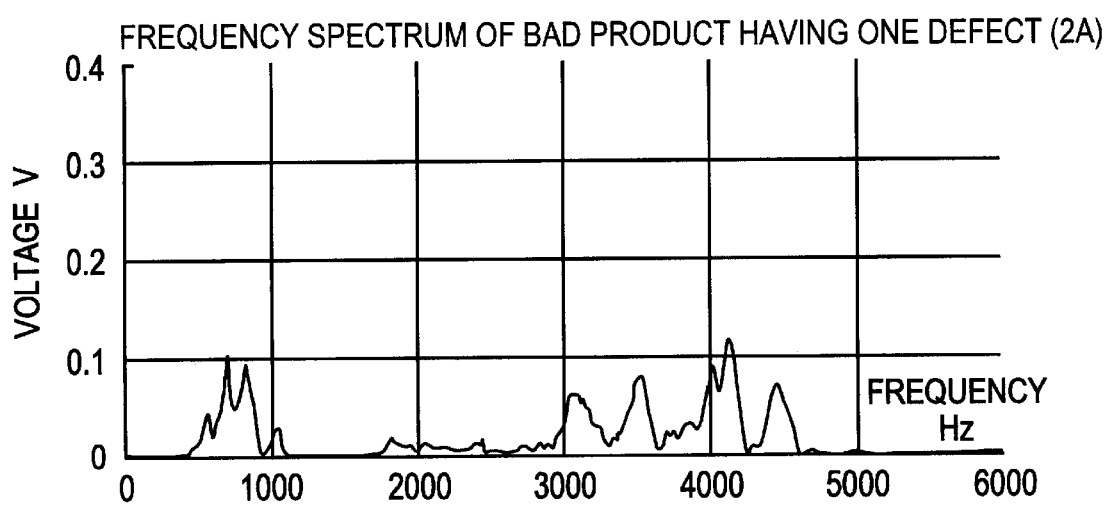
FIG. 11 is a graph showing a frequency spectrum of another bad product with one defect in a communicating hole.

In this way, an actual inspection is conducted with an apparatus shown in FIG. 1 after the network learns the frequency spectrum of a good product, the frequency spectrum of a bad product having two defects, and the frequency spectrum of a bad product having one defect and the like. The frequency spectrum shown in FIG. 8 is that of an inspected product that is good. The frequency spectrum shown in FIG. 9 is that of an inspected product that is bad with two obstructions. The frequency spectrum shown in FIG. 10 is that of an inspected product that is bad with one obstruction. The frequency spectrum shown in FIG. 11 is that of a bad product with one obstruction, which differs from the frequency spectrum of the bad product shown in FIG. 10. Determining the quality of these with the neural network enables the deviation to be acceptable, making it possible to improve inspection accuracy and speed. Determining quality in this way, then, a cylinder head S that was determined to be good is shipped to the next process as a good product, while a cylinder head S that was determined to be bad is eliminated from the process as a bad product.

Figure 7:
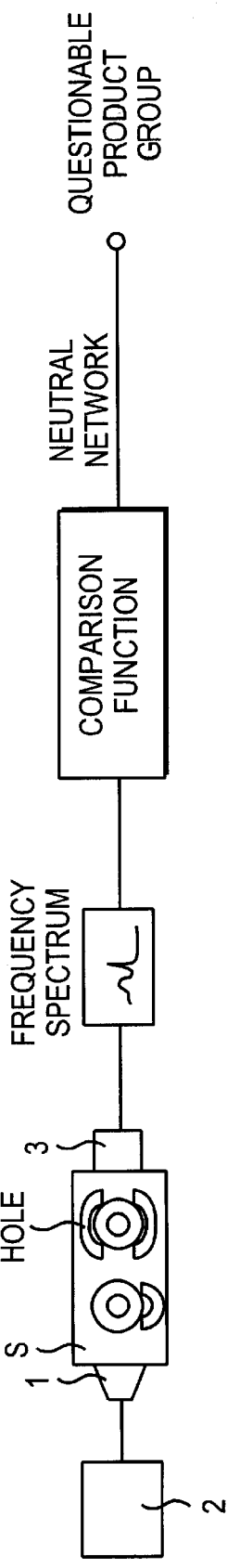
FIG. 7 is an explanatory view of a state in which quality can not be determined by the neural network.

However, there are cases in which an output value is output for a cylinder head S cast in large quantity which is neither for a good product nor a bad product. For example, assuming that the output value at the output layer 12a as a good product is 0.3, and the output value at the output stage 12b as a bad product is 0.23, it is difficult to determine whether the inspected product is good or bad from those values. In a case such as this, an operator will determine the inspected product to be a "questionable product" (see FIG. 7). Further, cylinder heads S at high and low temperatures, depending on the air temperature, are mixed together in the casting line. This variation of temperature causes the frequency characteristics to move in the frequency direction (along the horizontal axis in FIGS. 8 through 11). Therefore at this time, a cross-correlation function is obtained by means of the computing and processing device 6 and corrections are made, or the temperature of the cylinder head S is measured and corrections are done via the computing and processing device 6.

Note that in the above-mentioned preferred embodiment, the neural network is used to determine quality such that the speed and accuracy of the quality determination is improved. However, when accuracy and speed are not required, the quality may of course also be determined based on the peak value of the frequency spectrum with a computing and processing device, without using a neural network. Also, in the preferred embodiment, the audible sound waves are swept from 1 Hz to 6,000 Hz in accordance with the diameter of the communicating hole to be inspected. However, measurements may of course also be taken sweeping the audible sound waves from 1 Hz to 2,000 Hz, depending on the diameter of the communicating hole. Moreover, in the preferred embodiment the frequency is swept from low to high. Conversely it may also be swept from high to low. Also in the preferred embodiment, a single transmitter 1 and a single receiver 3 are provided, but a plurality of transmitters 1 and receivers 3 may also be provided, such that audible sound waves from a single transmitter 1 are received by a plurality of receivers 3 or audible sound waves from a plurality of transmitters 1 are combined and the resulting composite sweeping waveform is transmitted and then received by one or a plurality of receivers 3. Accordingly information regarding corners and complex flow passages and micro-pores and the like of the communicating hole is able to be obtained, improving the inspection accuracy even more. In addition, in the above-mentioned preferred embodiment, the transmitter 1 and the receiver 3 were disposed at both ends of the cylinder head S. A local inspection may of course also be conducted by disposing the transmitter 1 and the receiver 3 suitably within a communicating hole.

The present invention has various advantages such as that it enables an inspection to be conducted using sound waves which was difficult in the past, by emitting audible sound waves from one end of a communicating hole, receiving the audible sound waves which passed through the communicating hole, computing and processing the frequency spectrum of the audible sound waves based on a reference frequency spectrum, and determining the quality of the communicating hole. Further, because audible sound waves, which expand as opposed to ultrasound, are transmitted, it is possible to inspect a wide region of the communicating hole. Also, sweeping the frequency enables an accurate inspection to be conducted even with communicating holes having different size hole diameters, and setting a frequency of the audible sound waves to the value from 1 to 20,000 Hz enables the inspection to be done on products having holes with diameters of various sizes. Moreover, determining the quality with the neural network improves inspection speed as well as enhances the inspection accuracy, and determination is able to be facilitated and inspection efficiency improved by deeming a product which has a low probability when matched with the target value of good product bad. Furthermore, providing a plurality of transmitters enables a variety of combinations of sweeping waveforms to be created. Accordingly, information is able to be obtained regarding corners and complex portions or narrow portions and the like of a communicating hole which are in separate locations, thereby improving measurement accuracy. Moreover, providing a plurality of receivers increases the amount of information able to be obtained, therefore improving the reliability of quality determination.

What is claimed is:

1. A method of inspecting a communicating hole of a cast molded article, comprising the steps of:

providing a sound transmitter configured to be abutted against a surface entrance of a communicating hole of a cast molded article, said communicating hole including a plurality of entrance and exit holes;

providing a sound receiver configured to be abutted against a surface exit of said communicating hole;

emitting an audible sound wave from said sound transmitter;

receiving by said sound receiver the emitted audible sound wave that has passed through said communicating hole; and determining quality of the communicating hole by computing and processing a frequency spectrum of said received audible sound wave based on a reference frequency spectrum.

2. The method of inspecting a communicating hole of a cast molded article according to claim 1, further comprising the step of:

sweeping an audible sound wave emitted from a transmitter from a low frequency to a high frequency or from a high frequency to a low frequency.

3. The method of inspecting a communicating hole of a cast molded article according to claim 1, wherein an audible sound wave emitted from said transmitter is an audible sound wave of a frequency of 1 to 20,000 Hz.

4. The method of inspecting a communicating hole of a cast molded article according to claim 1, wherein said computing and processing computes and processes a frequency spectrum of said received audible sound wave by means of a neural network.

5. The method of inspecting a communicating hole of a cast molded article according to claim 4, wherein said computing and processing outputs a value corresponding to a probability that an inspected product is good or bad as an output value and determines quality of the communicating hole based on this output value.

6. An apparatus for inspecting a communicating hole of a cast molded article, comprising:

a transmitter of an audible sound wave configured to be abutted against an entrance of a communicating hole in a cast molded article, said communicating hole including a plurality of entrance and exit holes;

a receiver configured to be abutted against said communicating hole for receiving the audible sound wave from the transmitter that has passed through the communicating hole; and a computing and processing device for determining quality of the communicating hole by computing and processing a frequency spectrum of the audible sound wave received by said receiver based on a reference frequency spectrum.

7. The apparatus for inspecting a communicating hole of a cast molded article according to claim 6, wherein said transmitter sweeps said audible sound wave from a low frequency to a high frequency or from a high frequency to a low frequency.

8. The apparatus for inspecting a communicating hole of a cast molded article according to claim 6, wherein said transmitter emits an audible sound wave of a frequency of 1 to 20,000 Hz.

9. The apparatus for inspecting a communicating hole of a cast molded article according to claim 6, wherein said computing and processing device computes and processes a frequency spectrum of said received audible sound wave by means of a neural network.

10. The apparatus for inspecting a communicating hole of a cast molded article according to claim 9, wherein said computing and processing device outputs a value corresponding to a probability that an inspected product is good or bad as an output value.

11. The apparatus for inspecting a communicating hole of a cast molded article according to claim 10, further comprising:

a plurality of transmitters and/or receivers; and wherein said computing and processing device determines quality of a communicating hole based on a frequency spectrum of an audible sound wave sent and received between said plurality of transmitters and/or receivers.

* * * * *